United States Patent [19]

Imamura et al.

[11] Patent Number: 4,903,705
[45] Date of Patent: Feb. 27, 1990

[54] DIGITAL RADIOGRAPHY APPARATUS

[75] Inventors: Kazushi Imamura, Kashiwa; Masami Kamiya, Noda, both of Japan

[73] Assignee: Hitachi Medical Corporation, Tokyo, Japan

[21] Appl. No.: 259,426

[22] Filed: Oct. 11, 1988

Related U.S. Application Data

[63] Continuation of Ser. No. 795,442, Nov. 6, 1985, abandoned.

[30] Foreign Application Priority Data

Nov. 9, 1984 [JP] Japan ................. 59-236050

[51] Int. Cl.$^4$ ............................................. A61B 6/00
[52] U.S. Cl. .................................................. 128/654
[58] Field of Search ............... 364/414; 119/653, 659, 119/660-661; 358/111; 378/94, 95, 41-42

[56] References Cited

U.S. PATENT DOCUMENTS

| 3,871,360 | 3/1975 | Van Horn et al. | 128/671 |
| 3,954,098 | 5/1976 | Dick et al. | 128/661 X |
| 4,182,311 | 1/1980 | Seppi et al. | 128/653 |
| 4,245,647 | 1/1981 | Randall | 128/659 |
| 4,366,820 | 1/1983 | Heyda et al. | 128/659 |
| 4,413,630 | 11/1983 | Anderson et al. | 128/661 |
| 4,547,892 | 10/1985 | Richey et al. | 128/653 X |
| 4,585,008 | 4/1986 | Jarkewicz | 128/654 |
| 4,611,340 | 9/1986 | Okazaki | 128/708 X |
| 4,662,379 | 5/1987 | Macovski | 128/653 |
| 4,729,379 | 3/1988 | Ohe | 128/654 |

FOREIGN PATENT DOCUMENTS

| 12353 | 10/1984 | Japan | 128/654 |
| 231985 | 12/1984 | Japan | 128/654 |
| 0050900 | 3/1985 | Japan | 128/654 |

OTHER PUBLICATIONS

Hirji, M. et al., "EKG-Gated DISA in the Detection of Pulmonary Emboli", Radiology 1984, vol. 152, pp. 19-22.
Ozaki, T. et al., "DSA Device" Jap. Kokai Pat. Pub. No. 59-192353, publ. Oct. 31, 1984 as translated by USPTO on 10/1/87.
Fujii, C. et al., "X-Ray Diagnostic Device", Jap. Publ No. 59-231985, issued 23 Dec. 1984 as translated by USPTO on 11/1987 as PTO #5319.

Höhne, K. H. (editor), "Digital Image Processing in Medicine", Proceedings Hamburg 10-5-81, Springer-Verlag N.Y. 1981, pp. 1-41, 196-197.
Höhne, K. H., "Digital Image Processing in Medicine", Proceedings Hamburg 10-5-81, Springer-Verlag, N. Y. 1981.
Ovitt, T. et al., "Development of A Digital Video Subtraction System for Intravenous Angiography", Proc. Soc. Photo-Opt. Instr. Engrg, vol. 206 (1979), pp. 73-76.
Alpert, N. A. et al., "Non-Invasive Nuclear Kinecardiography", Jrnl Nuclear Medicine, vol. 15, No. 12, pp. 1182-1184.

Primary Examiner—Francis Jaworski
Attorney, Agent, or Firm—Sixbey, Friedman, Leedom and Ferguson

[57] ABSTRACT

A device for obtaining an image of a subject including a signal generating device including, for example, an X-ray generator for obtaining a signal representative of the subject, a detecting device for detecting a predetermined phase such as the R-wave of the electrocardiographic waveform of the subject, and an actuating device responsive to the detecting device for actuating the X-ray generator in substantial synchronism with the occurrence of the predetermined phase of the electrocardiographic waveform to thereby obtain the image of the subject. The device may include control circuitry for operating the detecting device, the actuating device and X-ray generator in the foregoing order to obtain a mask image of the subject, a device for storing the mask image, a device for injecting a contrast medium into the subject; a device for repeating the above operation of the detecting device, the actuating device, and the X-ray generator in the foregoing order to obtain a live image of the subject, and a device for subtracting the mask image and the live image with respect to each other to obtain a subtraction image to thereby eliminate motion-artifacts due to heartbeats of the subject, although subtraction angiography need not be employed. Different modes of operation of the device are also disclosed.

4 Claims, 4 Drawing Sheets

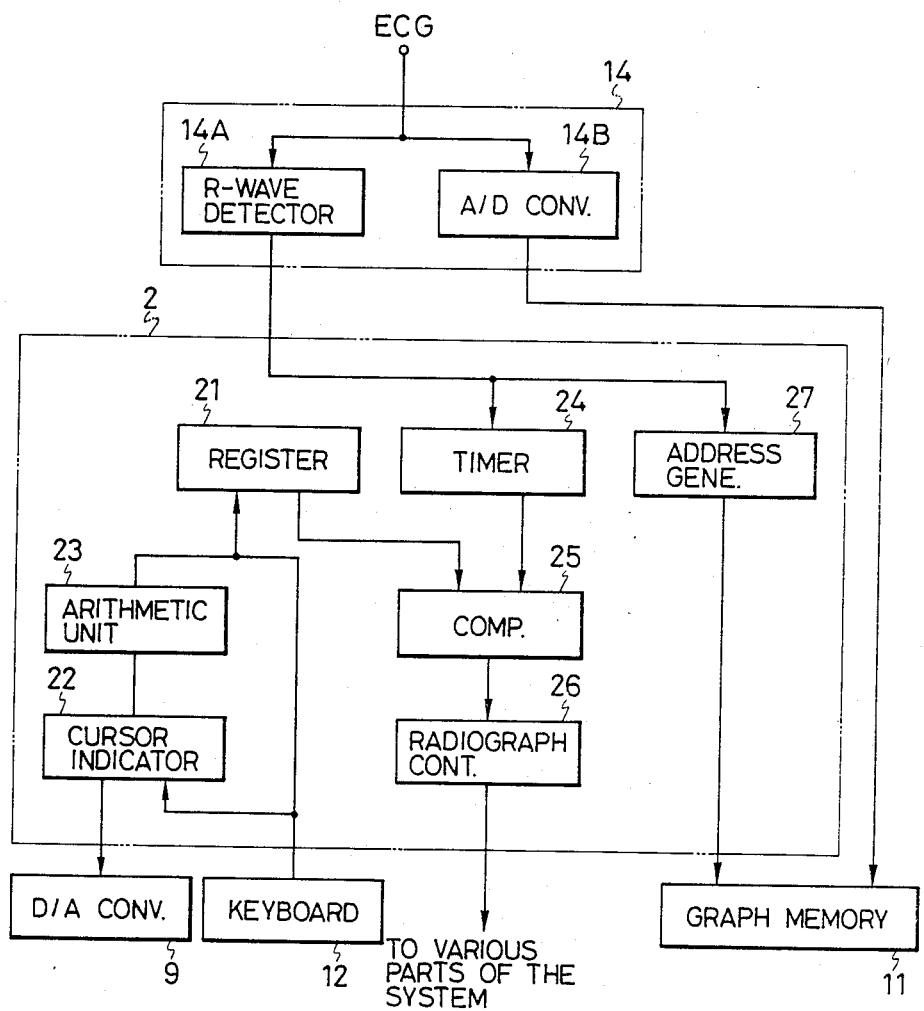

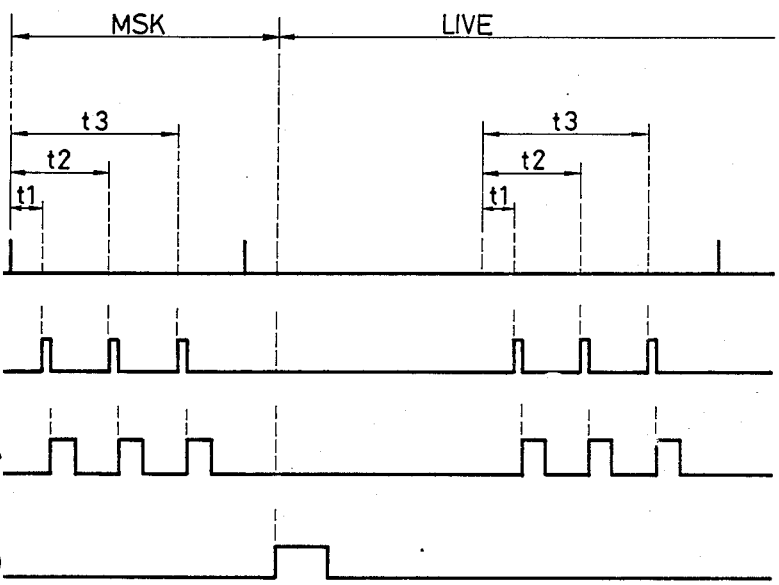
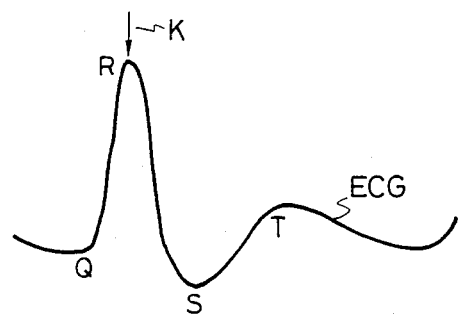

DIGITAL RADIOGRAPHY APPARATUS

This application is a continuation of Ser. No. 795,442, filed Nov. 6, 1985, now abandoned.

BACKGROUND OF THE INVENTION

1. Field of the Invention

The present invention relates to digital radiography apparatus, and in particular, to apparatus such as digital subtraction angiography apparatus (hereinafter abbreviated to "DSA apparatus"), used in angiography, cardiography, or the like, for radiographing of subjects such as the heart, the aorta, or the like, moved by heartbeats or the like.

2. Description of the Prior Art

In radiographing by DSA apparatus, even slight motion of a subject may form a motion-artifact so as to greatly deteriorate the quality of an image. Therefore, conventionally, in radiographing a rapidly moving heart, images for about one stroke were averaged to make a masking image so as to reduce motion-artifacts.

However, the method provided no essential solution for the problem. Although the images according to the method have been used to obtain a moving picture in practice, subjects such as a coronary artery and the like could not be represented without using risky means such as selective angiography, or the like.

SUMMARY OF THE INVENTION

An object of the present invention is to provide a technique by which fine X-ray images of a subject such as a coronary artery, or the like, can be obtained by reducing motion-artifacts of X-ray images of rapidly moving subjects due to heartbeats without using risky selective angiography, in a digital X-ray photographing apparatus such as DSA apparatus or the like.

The foregoing and other objects and novel features of the invention will be apparent by reference to the description, taken in connection with the accompanying drawings.

BRIEF DESCRIPTION OF THE DRAWINGS

FIGS. 1 to 5 are diagrams for explaining an embodiment of the DSA apparatus according to the present invention, in which:

FIG. 1 is a block diagram showing an illustrative schematic construction of a DSA apparatus;

FIG. 2 is a block diagram showing an illustrative detailed construction of the control unit shown in FIG. 1;

FIG. 3 is a time chart for explaining first and second operational procedures of the DSA apparatus;

FIG. 4 is a graph showing an example of a display format of an electrocardiogram; and FIG. 5 is a time chart for explaining a third operational procedure of the DSA apparatus.

DETAILED DESCRIPTION OF PREFERRED EMBODIMENTS

Figure 1:
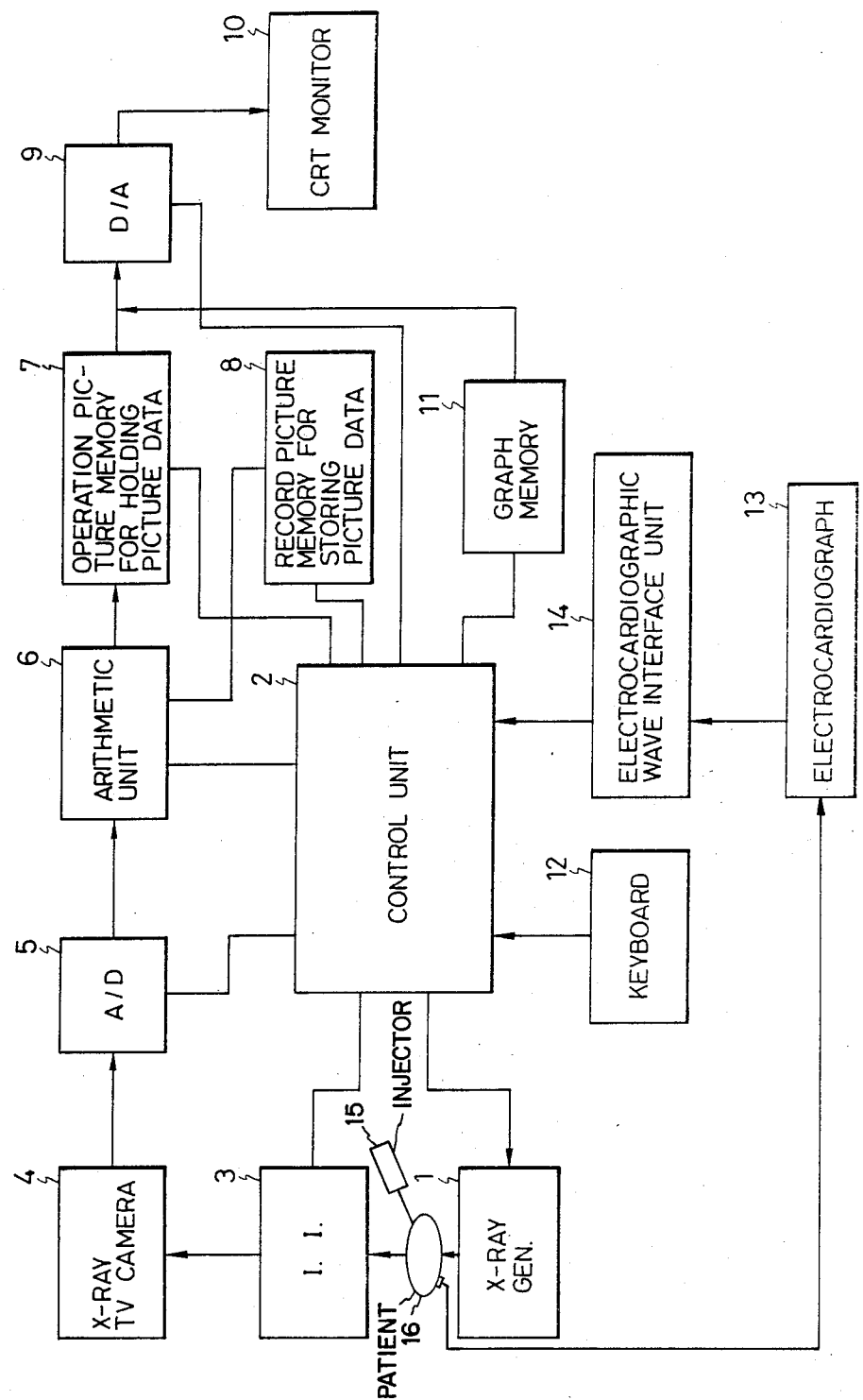

Referring to the drawings, the structural features of the present invention will be described in detail as to an embodiment of a DSA apparatus according to the invention hereunder. In all the drawings for explaining the embodiment, the parts having the same function are represented by the same reference numerals and repeated description with the same parts is omitted.

In FIG. 1 the reference numeral 1 designates an X-ray generator constituted by an X-ray tube, a high-voltage generator, etc., in which the setting of radiographic condition such as exposure time, X-ray tube current, X-ray tube voltage, etc., and the control such as an on-off control or the like are performed by a control unit 2 constituted by a computer, etc. The reference numeral 3 designates an image intensifier (hereinafter abbreviated to "I.I") for converting an X-ray transmission image of a subject 16 formed by X-rays irradiated to the subject from the X-ray generator 1, into an optical image. The reference numeral 4 designates an X-ray television camera for converting the optical image into a video signal. The reference numeral 5 designates an analog-to-digital (hereinafter abbreviated to "A/D") converter for converting the video signal into a digital signal (hereinafter referred to as "picture data"). The reference numeral 6 designates an arithmetic unit for performing operations such as addition, subtraction, multiplication, division, and the like, on the picture data. The reference numeral 7 designates an operation picture memory for holding picture data during operations of the arithmetic unit 6 or for holding picture data to be displayed. The reference numeral 8 designates a record picture memory for storing picture data after or before operations by the arithmetic unit 6. The reference numeral 9 designates a D/A converter for converting picture data into an analog video signal. The reference numeral 10 designates a display unit such as a CRT monitor or the like for displaying a picture or an electrocardiogram. The reference numeral 11 designates a graph memory which is used for the display of an electrocardiogram. The reference numeral 12 designates a keyboard by which an operator may perform setting of the timing of exposure or an indication of the start of radiographing. The reference numeral 13 designates an electrocardiograph for detecting electrocardiographic waveforms. The reference numeral 14 designates an electrocardiographic wave interface unit for A/D converting the electrocardiographic wave detected by the electrocardiograph 13 into a digital electrocardiographic signal (hereinafter referred to as "electrocardiographic data") and for detecting a standard point for the exposure timing in the electrocardiogram, for example, R-wave (FIG. 4). Control of each of the above-mentioned parts is effected by control unit 2.

FIG. 2 shows a detailed illustrative arrangement of the control unit 2 and the electrocardiographic wave interface unit 14.

In FIG. 2 the reference numeral 14A designates an R-wave detector in the electrocardiographic wave interface unit 14, by which the R-wave is detected to provide a standard point for exposure timing. The reference numeral 14B designates an A/D converter for converting the electrocardiographic waveform into the electrocardiographic data. The output electrocardiographic data from the A/D converter 14B is transmitted to the graph memory 11. The reference numeral 21 designates a register for holding the set-up exposure timing, for example, the exposure timing $t_1$, $t_2$, or $t_3$ shown in FIG. 3 and entered through the keyboard. The reference numeral 22 designates a cursor indicator for displaying the electrocardiogram stored in the graph memory 11 and for displaying an indication such as a cursor K(FIG. 4) or the like on the electrocardiogram at a desired phase to be exposed. The position of the cursor displayed by the cursor indicator 22 can be freely moved by the keyboard 12. The cursor signal of the cursor indicator 22 is entered into an arithmetic unit 23 so that a differential time $t_1$, $t_2$, or $t_3$ from the R-wave of the electrocardiogram is calculated on the basis of the displayed position of the cursor, and the result of calculation is applied to the register 21 to be held therein. On the other hand, the cursor signal is transmitted to the D/A converter 9 and the cursor K is indicated on the display unit 10. The reference numeral 24 designates a timer which is actuated to start by the R-wave detection signal of the R-wave detector 14A, and the output thereof is applied to a comparator 25. When the comparator 25 recognizes that exposure timing $t_1$, $t_2$, or $t_3$ set in the register 21 coincides with the output value of the timer 24, a timing signal is produced in synchronism with an electrocardiographic waveform showing the passage of time $t_1$, $t_2$, or $t_3$ after the detection of the R-wave. The timing signal is applied to a radiograph controller 26 so as to produce an exposure timing in accordance with the radiographing conditions, the exposure timing being transmitted to various parts of the system. The reference numeral 27 designates an address generator used for writing the electrocardiographic data to the graph memory 11, by which an address is given on basis of the R-wave.

Although the foregoing illustrates the case where the keyboard 12 is used for the purpose of moving the cursor K, a trackball, a joystick, or the like, may be used. Further, instead of the indication by means of the cursor K, a light pen or the like may be used for the indication.

Figures 5A, 5B, 5C, 5E, 5F, 5G:
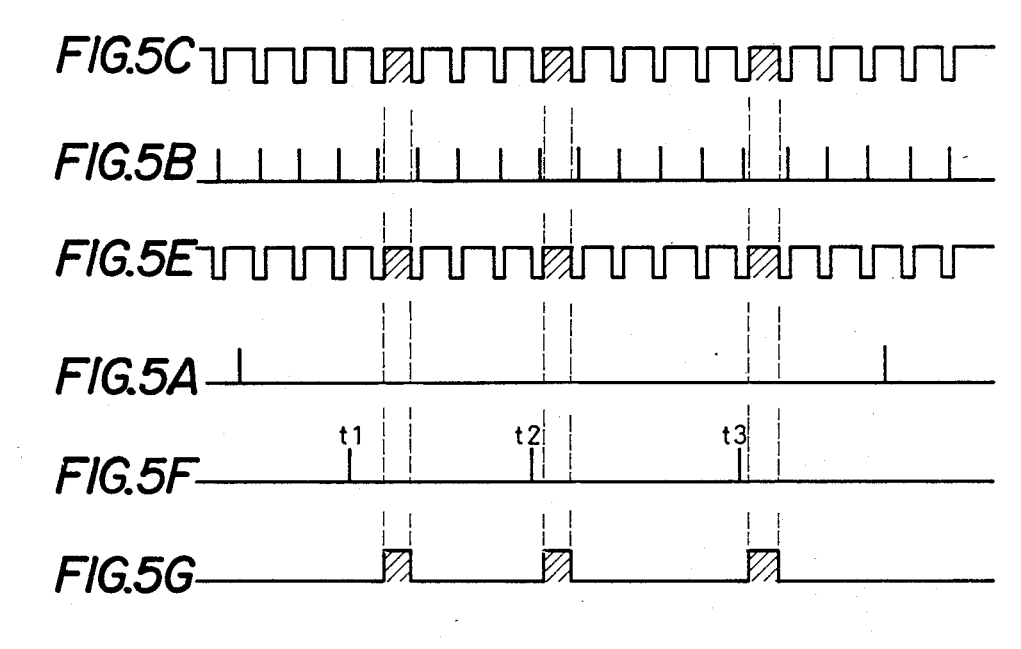

In FIGS. 3 and 5, the waveform (A) shows an R-wave detection signal, (B) an X-ray irradiation control signal, (C) a video signal, (D) a contrast medium injection control signal, (E) an operation control signal, (F) a set-up exposure timing signal, and (G) a picture data taken-in signal of the record picture memory 8. MSK represents the masking image radiographing period, LIVE the live image radiographing period, and $t_1$, $t_2$, and $t_3$ the periods of time.

In FIG. 4, ECG represents the electrocardiogram and K indicates the cursor.

Next, the embodiments of the DSA aparatus will be described in detail with reference to FIG. 1 through FIG. 5.

(I) First Operational Procedure

In FIGS. 1 to 4, when the time $t_1$, $t_2$, or $t_3$ from the R-wave to the X-ray irradiation is entered through the keyboard 12, the control unit 2 stores the received value in the internal register 21. Upon the input of a radiographing start command through the keyboard 12, the electrocardiographic wave interface unit 14 is operated and the R-wave is detected by the R-wave detector 14A. The timer 24 is started by the R-wave detection signal and the output thereof is applied to the comparator 25. The comparator 25 compares the output of the timer 24 with the exposure timing $t_1$, $t_2$, or $t_3$ set in the register 21 to detect the coincidence there-between. Upon detection of the coincidence, the comparator 25 produces a timing signal in synchronism with an electrocardiographic waveform at the point of time after a lapse of time $t_1$, $t_2$, or $t_3$ from the detection of the R-wave. The timing signal is applied to the radiograph controller 26 which in turn produces a exposure timing signal in accordance with the radiographing conditions. In response to this exposure timing signal, the X-ray generator 1 is operated to irradiate the subject with X-rays. The X-ray image of the subject obtained by the irradiation is converted into an optical image by the I.I.3, and the optical image is accumulated in a pickup tube within the X-ray television camera 4. After stopping X-ray irradiation, beam scanning of the X-ray television camera 4 is performed to take out the accumulated image as a video signal. The video signal is converted by the A/D converter 5 into a picture data which is stored as a masking image in the operational picture memory 7.

Next, a contrast medium is injected into the subject by a contrast medium injector 15, and a live image is radiographed in the same manner as the masking image. At this time, the arithmetic unit 6 performs subtraction between the live image and the masking image, both of which are equivalent in differential time $t_1$, $t_2$, or $t_3$ from the R-wave, depending on which differential time has been selected thereby making a subtraction image. The subtraction image is converted into a video signal by the D/A converter 9 and displayed on the display unit 10. The live image or subtraction image is stored in the record picture memory 8.

As seen in the foregoing, according to this embodiment of the invention, motion-artifacts owing to heartbeats can be eliminated by the subtraction between the masking image and the live image radiographed in the phase synchronized with the heartbeats. Accordingly, it is possible to radiograph and represent blood vessels such as a coronary artery, a peripheral pulmonary artery, or the like, having been invisible because of the heartbeats.

As a result, it is possible to enlarge the range of diagnostic regions in a patient.

(II) Second Operational Procedure

In FIGS. 1 through 4, although in the first operational procedure, there is used the most simple method in which a differential time from the R-wave is directly entered for the purpose of setting the exposure timing synchronized with the electrocardiographic waveform after a lapse of time $t_1$, $t_2$, or $t_3$ from the detection of the R-wave, that is, a method in which the control unit 2 stores the entered value as it is, in the second operational procedure, the electrocardiographic wave interface unit 14 is operated to receive the electrocardiographic waveform and the received electrocardiographic waveform is converted into an electrocardiographic data by the A/D converter 14B before starting the radiographing. The electrocardiographic data is stored in the graph memory 12. The electrocardiographic data stored in the graph memory 11 is converted into an analog signal by the D/A converter 9 and an electrocardiogram is displayed the display unit 10. The display has a format as shown in FIG. 4.

The operator operates the keyboard 12 to cause the cursor indicator 22 to move the cursor K, while observing the displayed electrocardiogram ECG. Since the electrocardiogram ECG is caused to correspond to the real exposure time on the basis of the sampling cycle of the A/D converter 14B in the electrocardiographic wave interface unit 14, the set-up exposure timing is determined by calculating the differential time $t_1$, $t_2$, or $t_3$ from the R-wave by the arithmetic unit 23 on the basis of the amount of displacement of the cursor K or the relative position between the electrocardiogram ECG and the cursor K. This is entered into the register 21 and set therein. The operations after the exposure timing has been set in the register 21 are the same as the first operational procedure.

According to the second operational procedure, the operator can set a exposure timing without paying attention to the relation between the electrocardiogram and the real exposure time, so that it is possible to radiograph accurately and quickly.

For example, in the first operational procedure in which the exposure timing from the R-wave is directly set, it is impossible to synchronize the photographic timing with a desired phase such as systole, diastole, or the like. In the second operational procedure, on the contrary, it is possible to easily set the exposure timing so that it is synchronized with the electrocardiography merely be setting a desired exposure phase with the cursor while displaying the electrocardiogram.

(III) Third Operational Procedure

Although in the first and second procedures, the radiographing is performed only in synchronism with the electrocardiographic waveform, it is possible to perform radiographing in a continuous mode in accordance with the time chart of FIG. 5 by using the same system structure as FIG. 1.

The X-ray irradiation, video signal, and arithmetic operation are effected in the same way as a conventional continuous imaging mode; however, the operation after detecting the R-wave 8F or the like distinguishes this embodiment. As either the masking image or live image is radiographed by the same process, this third operational procedure will be described, on one hand, omitting the contrast medium injection step and related steps.

The third operational procedure will be described with reference to FIGS. 1 and 5.

The X-ray television camera 4 continuously performs scanning and produces a video signal. The X-rays are irradiated during the blanking period of this scanning. Arithmetic operations are performed for every frame of the thus obtained picture data, and the result is displayed on the display unit 10. In such continuous mode radiographing, the R-wave detection is performed and the foregoing first or second operational procedure is applied, to thereby set a exposure timing synchronized with the electrocardiographic waveform. Only the picture data in the thus set exposure timing is stored in the record picture memory 8. In this case, since the X-ray television camera 4 is continuously caused to perform scanning, the radiographing operations, such as the X-ray irradiation, video signal, arithmetic operation, etc., are not always synchronized with the set exposure timing. Therefore, the picture data to be stored in the record picture memory 8 is determined to be, for example, the first frame of picture data after a lapse of time of the set exposure timing (the hatched portion FIG. 5).

As described above, according to this third operational procedure, it is possible to obtain two different mode images at the same time n which one is a moving image owing to the continuous imaging mode and another is a detailed picture image owing to the synchronization with the electrocardiogram wave when the exposure timing synchronized with the electrocardiographic waveform is set in the same way as in the first or second operational procedure, so that it is possible to obtain high diagnostic information. Moreover, it is possible to reduce the number of examinations for a patient, thereby reducing risk caused by such examinations.

Although the X-ray irradiation may be performed during the blanking of the video signal in the third operational procedure, continuous X-ray irradiation may, of course, also be utilized.

As described above, according to the invention, it is possible to obtain the following effects or advantages:

(1) It is possible to perform an arithmetic operation between picture images in phase with respect to the movement of the heart by radiographing synchronously with the electrocardiographic waveform, and therefore it is possible to reduce motion-artifacts of the X-ray picture of a subject due to rapidly moving heartbeats;

(2) It is possible to represent regions such as a coronary artery, a peripheral pulmonary artery, and the like, owing to the advantage described above in the paragraph (1);

(3) It is possible to enlarge the range of diagnostic regions of a patient, owing to the above-mentioned advantage described in the paragraph (1);

(4) It is possible to obtain a moving image by radiographing in the continuous imaging mode and a detailed picture can be obtained by photographing in synchronism with the electrocardiogram, if the photographing timing synchronized with the electrocardiographic waveform is set in the same manner as the operational procedure described in the foregoing paragraph (1), and therefore it is possible to obtain high diagnostic information;

(5) It is possible to reduce the number of tests for a patient owing to the advantage described in the paragraph (1), and therefore it is possible to suppress risks caused bu such tests.

While the invention has been described with respect to the above preferred embodiments, it is to be understood that the invention is not limited to the foregoing specific embodiments but various changes and modifications may be made to the embodiments without departing from the spirit and scope of the invention.

For example, it is a matter of course that the present invention is applicable to a digital radiography apparatus other than a DSA apparatus as shown in the foregoing embodiments.

What is claimed:

1. A digital radiography apparatus comprising:
   electrocardiographic wave detecting means for detecting electrocardiographic waves of a subject before and during an X-ray photographing operation, and means for converting the waveforms of the electrocardiographic waves into signals for display;
   contrast medium injection means for injecting contrast medium into a portion of the subject to be photographed with X-rays;
   X-ray photographing means for irradiating the subject with X-rays and generating an optical X-ray image of the portion of the subject to be photographed;
   means for controlling said contrast medium injection means and said X-ray photographing means and generating images at predetermined times both before and after injection of the contrast medium into the subject;
   means for converting the X-ray images before and after injection of the contrast medium into the subject into television signals in time-series;
   means for successively converting the television signals to digital signals and performing a subtraction operation between the digital signals before and after injection of the contrast medium into the subject;
   display means for displaying a resultant X-ray image obtained through the subtraction operation and the waveform of the electrocardiographic wave detected by said electrocardiographic wave detecting means; means for inputting a marker on the displayed waveform of the electrocardiographic wave with a cursor; and means for detecting a specific wave phase in the electrocardiographic wave and setting the timing for the X-ray photographing operation based upon the position of the cursor relative to the position of the specific wave phase.

2. A digital radiographic apparatus comprising:

electrocardiographic wave detecting means for detecting an electrocardiographic wave of a subject and outputting a detection signal in response to detection of a specific wave phase in the electrocardiographic wave;

contrast medium injection means for injecting contrast medium into the portion of the subject to be photographed with X-rays;

means for setting a desired lapse time from an instant in time when a specific wave phase occurs;

X-ray photographing means for irradiating the subject with X-rays and generating an optical X-ray image of the portion of the subject to be photographed;

means for controlling said contrast medium injection means and said X-ray photographing means and generating X-ray images at predetermined times both before and after injection of the contrast medium into the subject;

means for converting the X-ray images before and after injection of the contrast medium into the subject into television signals in time-series;

means for successively converting the time-series television signals into digital signals and performing a subtraction operation between the digital signals before and after injection of the contrast medium into the subject;

display means for displaying a resultant X-ray image obtained through the subtraction operation; and means for actuating said electrocardiographic wave detecting means in response to a photography starting signal and applying an X-ray radiation instruction signal to said X-ray photographing means when a time elapsing from the occurrence of the detection signal in said electrocardiographic detecting means corresponds to a desired lapse time.

3. A digital radiography apparatus comprising:

electrocardiographic wave detection means for detecting electrocardiographic waves of a subject before and during the X-ray photographing operation and converting the waveforms of the electrocardiographic waves into signals for a display;

contrast medium injection means for injecting contrast medium into a portion of the subject to be photographed with X-rays;

X-ray photographing means for irradiating the subject with X-rays and generating na optical X-ray image of the portion of the subject to be photographed;

means for controlling said contrast medium injection means and said X-ray photographing means, and generating X-ray images both before and after injection of the contrast medium into the subject while X-rays are substantially continuously irradiated;

means for converting the X-ray images before and after injection of the contrast medium into the subject into television signals;

means for successively converting the television signals to digital signals and performing a subtraction operation between the digital signals before and after injection of the contrast medium into the subject;

display means for displaying a resultant X-ray image obtained through the subtraction operation and the waveform of the electrocardiographic wave detected by said electrocardiographic wave detecting means;

meant for inputting a marker on the displayed waveform of the electrocardiographic wave with a cursor;

means for detecting a specific wave phase in the electrocardiographic wave and extracting only the digital signals corresponding to the position of the cursor relative to that of the specific wave phase; and means for subjecting to the subtraction operation the extracted digital signals before and after injection of the contrast medium into the subject.

4. A digital radiographic apparatus comprising:

electrocardiographic wave detection means for detecting an electrocardiographic wave of a subject, and outputting a detection signal in response to detection of a specific wave phase in the electrocardiographic wave;

contrast medium injection means for injecting contrast medium into a portion of the subject to be photographed with X-rays;

means for setting a desired time lapse from the instant time when the specific wave phase occurs;

X-ray photographing means for irradiating the subject with X-rays, and generating an optical X-ray image of the portion of the subject to be photographed;

means for controlling said contrast medium injection means and said X-ray photographing means, and generating X-ray images both before and after injection of the contrast medium into the subject while X-rays are substantially continuously irradiated;

means for converting the X-ray images before and after injection of the contrast medium into the subject into television signals;

means for successively converting the television signals into digital signals, and performing a subtraction operation between the digital signals before and after injection of the contrast medium into the subject;

display means for displaying a resultant X-ray image obtained through the subtraction operation;

means for actuating said electrocardiographic wave detecting means in response to a photography starting signal, and extracting from the digital signals only the digital signals at the time when a time elapsing from the occurrence of the detection signal in said electrocardiographic detecting means corresponds to a desired lapse time; and means for subjecting to the subtraction operation the extracted digital signals before and after injection of the contrast medium into the subject.

* * * * *